United States Patent [19]

Stillings

[11] Patent Number: 4,782,072

[45] Date of Patent: Nov. 1, 1988

[54] THIADIAZOLE DERIVATIVE

[75] Inventor: Michael R. Stillings, Hull, Great Britain

[73] Assignee: Reckitt & Colman Products Limited, London, Great Britain

[21] Appl. No.: 113,076

[22] Filed: Oct. 27, 1987

[30] Foreign Application Priority Data

Oct. 28, 1986 [GB] United Kingdom ............... 8625774

[51] Int. Cl.$^4$ .................... C07D 285/12; A61K 31/41
[52] U.S. Cl. ..................................... 514/363; 548/136
[58] Field of Search ........................ 548/136; 514/363

[56] References Cited

FOREIGN PATENT DOCUMENTS 2805756  8/1979  Fed. Rep. of Germany ...... 548/136

OTHER PUBLICATIONS

Stillings et al, J. Med. Chem. 29, 2280 (1986).

Primary Examiner—Robert Gerstl
Attorney, Agent, or Firm—Bacon & Thomas

[57] ABSTRACT

2-Aminomethyl-5-(2-biphenylyl)-1,3,4-thiadiazole and is non-toxic salts.

Processes for the preparation and pharmaceutical compositions thereof. The compound exhibits anticonvulsant activity and is indicated for the use in the treatment of epilepsy.

6 Claims, No Drawings

THIADIAZOLE DERIVATIVE

This invention relates to a thiadiazole derivative, its non-toxic salts, processes for its preparation and pharmaceutical compositions of the derivative or its salts.

According to this invention there is provided 2-aminomethyl-5-(2-biphenylyl)-1,3,4-thiadiazole of Formula 1

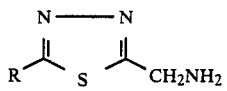

wherein R is 2-biphenylyl and its non-toxic salts.

The invention also includes pharmaceutical compositions comprising the compound of Formula 1 or a non-toxic salt thereof together with a pharmaceutically acceptable diluent or carrier.

Examples of non-toxic salts are those with inorganic acids such as hydrochloric acid, sulphuric acid or phosphoric acid or organic acids such as acetic, propionic, malonic, succinic, fumaric, tartaric, citric or cinnamic acid.

The compound of Formula 1 has been shown in animal tests to exhibit potent anticonvulsant activity.

The invention also includes the use of the compound of Formula 1 or a non-toxic salt thereof for the manufacture of a medicament for the treatment of epilepsy and a method of treating epilepsy which comprises administering to a patient suffering from epilepsy an effective amount of the compound of Formula 1 or a non-toxic salt thereof.

The compound of Formula 1 may be prepared from the compound of Formula 2

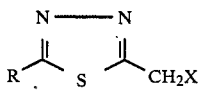

in which R is as hereinbefore defined and X is chloro or bromo by reaction with potassium phthalimide followed by the reaction of the resultant product with hydrazine hydrate.

The compound of Formula 2 may be prepared according to the following reaction sequence:

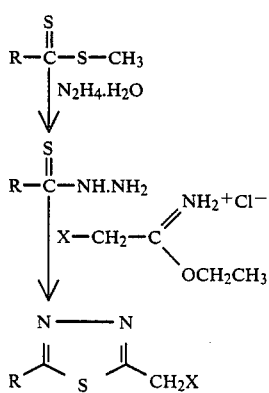

The invention is illustrated by the following Example. Melting points were determined on a Kofler hot stage apparatus or a Buchi apparatus in glass capillary tubes and are uncorrected.

EXAMPLE

2-Aminomethyl-5-(2-biphenylyl)-1,3,4-thiadiazole

2-Iodobiphenyl (20.0 g) was added to a stirred mixture of dry diethyl ether (75 ml) and magnesium (1.9 g). After 5 min. a vigorous reaction ensued. When this had subsided, the mixture was stirred at reflux for 1 hour. After it had been cooled, the Grignard solution was decanted from the small quantity of magnesium remaining and added dropwise to a solution of carbon disulfide (5.0 g) in dry diethyl ether (25 ml). The mixture was stirred at room temperature for 2.5 h after which methyl iodide (11.0 g) in dry tetrahydrofuran (25 ml) was added over 5 min. The resultant bright yellow suspension was stirred at reflux for 1 hour, a further portion of methyl iodide (5.0 g) was added and the reaction continued for 1 hour. The mixture was cooled and partitioned between ethyl acetate and water. The organic layer was washed with water, dried ($MgSO_4$) and evaporated to dryness to give methyl 2-biphenylyldithiobenzoate as a red-brown oil: yield 14.2 g (83%).

A mixture of the dithiobenzoate (14.2 g) and hydrazine hydrate (98%, 11.0 g) was dissolved in ethanol (100 ml) and heated at reflux for 1 hour. The majority of the ethanol was then distilled off under reduced pressure and the residue was partitioned between ethyl acetate and water. The organic layer was washed with water, dried ($MgSO_4$) and evaporated to give an oily solid which was triturated with petroleum ether (bp 40–60%°C.)/diethyl ether to give 2-biphenylylthiohydrazide as a yellow solid: yield 9.9 g (75%).

A solution of chloroacetonitrile (10.0 g), ethanol (6.8 g) and dry diethyl ether (76 ml) was stirred and cooled at 0° C. while a stream of dry HCl gas was bubbled through. After 0.5 h the white crystalline imidate salt had precipitated. Excess dry diethyl ether was added to the mixture which was then filtered. The solid was washed with dry ether and stored over $P_2O_5$ in vacuo. The yield of imidate hydrochloride was 20.0 g (97%); mp 89° C. (dec).

A mixture of the imidate salt (9.0 g) and 2-biphenylylthiohydrazide (9.9 g) in ethanol (103 ml) was heated under reflux for 0.5 h. The ethanol was removed under reduced pressure and the residue was partitioned between ethyl acetate and water. The organic layer was washed with water, dried ($MgSO_4$) and evaporated to give crude 2-biphenylyl-5-chloromethyl-1,3,4-thiadiazole as a red solid: yield 11.3 g (91%).

A mixture of the crude chloromethylthiadiazole (1.5 g) potassium phthalimide (0.96 g) and dry dimethylformamide (7.5 ml) was stirred and heated at 50°–70° C. for 1 hour. The resulting solution was cooled and partitioned between ethyl acetate and water and the organic layer was washed with 0.2N NaOH, water and dried ($MgSO_4$). Evaporation gave a dark brown gum which was purified via column chromatography on silica eluting with chloroform to give 2-biphenylyl-5-N-phthalimidomethyl-1,3,4-thiadiazole as a light brown solid: yield 1.0 g (63%).

A mixture of the phthalimide (1.0 g) hydrazine hydrate (98%, 0.16 g) and ethanol (7 ml) was heated under reflux. After 5 min. the reaction mixture became solid; heating was continued for 0.5 h. After it had cooled, the mixture was partitioned between diethyl ether (10 ml) and aqueous KOH solution 10%, 1.0 g). The ether layer was separated off, washed with water, dried (MgSO$_4$) and evaporated to give a solid which was converted to a hydrochloride salt using ethanol and ethereal HCl. The resulting white solid was crystallised from ethanol/diethyl ether to give 2-aminomethyl-5-(2-biphenylyl)-1,3,4-thiadiazole hydrochloride yield 0.42 g (43%); mp 222°–223° C. (dec).

The pharmacological activity of the compound of the invention has been determined according to the following procedures. Its anticonvulsant activity was determined in the metrazol antagonism test in both mice and rats (MMS) (Soaje-Echaque E; Lim RKS, *J Pharmac Exp Ther* 1962, 138, 224; Desmedt LKC; Niemegeers CJE; Lewi PJ; Janssen PAJ, *Arzneim-Forsch* (Drug Res), 1976, 26, 1592) and the electroshock test (MES) (Perry JK; Tower DB; Woodbury DM; Walter RD, "Experimental Models of Epilepsy", editor Purpura DP; Raven Press: New York, 1972, 434).

Table 1 shows the effects of the compound on maximal electroshock seizures (MES) and maximal metrazol seizures (MMS) in the mouse and rat compared with three established anticonvulsant drugs after oral administration at t=1 hour.

TABLE 1

| | ED$_{50}$ mg/kg (limits) | | | |
| | RAT | | MOUSE | |
| COMPOUND | MES | MMS | MES | MMS |
|---|---|---|---|---|
| Example | 10(8–14) | 9(5–12) | 22(11–41) | 20(9–27) |
| phenytoin | 14(6–23) | 12(9–16) | 8(4–12) | 8(6–11) |
| phenobarbital | 9(7–13) | 4(2–5) | 12(9–15) | 4(3–6) |
| carbamazepine | 4(2–7) | 3(2–5) | 20(17–23) | 11(2–16) |

Table 2 shows the effect of the compound on MES in the mouse compared with phenytoin, phenobarbital and carbamazepine after i.p. administration.

TABLE 2

| | ED$_{50}$ mg/kg (limits) | |
| COMPOUND | MES at time of peak effect | Time of peak effect (min.) |
|---|---|---|
| Example | 7(5–8) | 10 |
| phenytoin | 8(4–9) | 60 |
| phenobarbital | 18(13–37) | 30 |
| carbamazepine | 6(4–8) | 20 |

From the Tables it can be seen that in the rat and the mouse the compound was a potent anticonvulsant, blocking both electrically and chemically induced seizures. It was effective by both the intraperitoneal and oral routes and the time of peak effect by both methods of administration was between ten and twenty minutes after dosing indicating a very rapid rate of absorption. Its potency was comparable with established anticonvulsant drugs in these tests.

An assessment of the neurotoxicity of the compound was carried out in mice using the rotarod test (Collier, HOJ; Fielier, EC; Hall, RA, *Analyst*, 1949, 74, 592). The data in Table 3 shows TD$_{50}$ values at the time of peak anticonvulsant effect obtained with the compound and the standard drugs after i.p. administration in the mouse. The protective index (PI) of the compound (TD$_{50}$ divided by ED$_{50}$ i.p. at time of peak effect) was 6.5; the corresponding values for phenytoin, phenobarbital and carbamazepine were 7, 4.8 and 11 respectively.

TABLE 3

| COMPOUND | TD$_{50}$[a] mg/kg po at 1 hour | TD$_{50}$ mg/kg ip at time of peak effect | PI[b] |
|---|---|---|---|
| Example | 318(230–471) | 45(23–68) | 6.5 |
| phenytoin | 216(154–239) | 56(27–74) | 7 |
| phenobarbital | 68(52–92) | 86(54–140) | 4.8 |
| carbamazepine | 166(104–282) | 67(29–108) | 11.1 |

[a]Dose at which 50% of trained animals fall off the rotarod.
[b]Protective index is calculated by dividing the TD$_{50}$ (ip at time of peak anticonvulsant effect) by the ED$_{50}$ under the same conditions (Table 2).

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of Formula I or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

Compositions for parenteral administration may be in the form of sterile injectable preparations such as solutions or suspensions in for example water, saline or 1,3-butane diol.

For the purpose of convenience and accuracy of dosing the compositions are advantageously employed in a unit dosage form. For oral administration the unit dosage form contains from 1 to 200 mg, preferably 5 to 100 mg of the compound of Formula 1 or a non-toxic salt thereof. Parenteral unit dosage forms contain from 0.1 to 25 mg of the compound of Formula 1 or a non-toxic salt thereof per 1 ml of the preparation.

The invention is further illustrated by the following Examples of compositions in which all parts are by weight.

EXAMPLE I

A mixture of one part 2-aminomethyl-5-(2-biphenylyl)-1,3,4-thiadiazole hydrochloride and four parts microcrystalline cellulose together with 1% of magnesium stearate is compressed into tablets. Conveniently the tablets are of such a size as to contain 5, 10, 25, 50 or 100 mg of the active ingredient.

EXAMPLE II

A mixture of one part 2-aminoethyl-5-(2-biphenylyl)-1,3,4-thiadiazole hydrochloride and four parts spray dried lactose together with 1% magnesium stearate is filled into hard gelatine capsules. The capsules may conveniently contain 5, 10, 25, 50 or 100 mg of the active ingredient.

We claim:

1. 2-Aminomethyl-5-(2-biphenylyl)-1,3,4-thiadiazole and its non-toxic salts.

2. A pharmaceutical composition for the treatment of epilepsy which comprises an effective amount for the treatment of epilepsy of the compound claimed in claim 1 or a non-toxic salt thereof, together with a pharmaceutically acceptable diluent or carrier.

3. A pharmaceutical composition as claimed in claim 2 in unit dosage form for oral administration comprising from 1 to 200 mg of the compound or a non-toxic salt thereof per unit dosage.

4. A pharmaceutical composition as claimed in claim 3 wherein each unit dosage form contains from 5 to 100 mg of the compound or a non-toxic salt thereof.

5. A pharmaceutical composition as claimed in claim 2 in unit dosage form for parenteral administration comprising from 0.1 to 25 mg of the compound or a non-toxic salt thereof per 1 ml of the composition.

6. A method of treating epilepsy which comprises administering to a patient suffering from epilepsy an effective amount of the compound claimed in claim 1 or a non-toxic salt thereof.

* * * * *